United States Patent [19]
Chigogidze

[11] Patent Number: 5,695,508
[45] Date of Patent: Dec. 9, 1997

[54] DEVICE AND METHOD FOR DYNAMIC DILATION OF HOLLOW ORGANS WITH ACTIVE PERFUSION AND EXTRACTION

[75] Inventor: Nikolay A. Chigogidze, Moscow, Russian Federation

[73] Assignees: Bakulev Institute of Cardio-Vascular Surgery, Moscow, Russian Federation; Vitas Corporation USA, New York, N.Y.

[21] Appl. No.: 648,562

[22] Filed: May 16, 1996

[30] Foreign Application Priority Data

Jun. 16, 1995 [US] U.S. .................................... 60/002244

[51] Int. Cl.$^6$ .................................................. A61B 17/22
[52] U.S. Cl. .................................................. 606/159; 606/1
[58] Field of Search .................................. 604/280, 281; 606/1, 127, 128, 159, 167, 180, 190, 191

[56] References Cited

U.S. PATENT DOCUMENTS

| | | |
|---|---|---|
| 4,646,736 | 3/1987 | Auth .................................. 606/159 |
| 4,706,671 | 11/1987 | Weinrib .................................. 606/159 |
| 5,269,751 | 12/1993 | Kaliman et al. ........................ 606/159 |

Primary Examiner—Glenn Dawson
Attorney, Agent, or Firm—Ilya Zborovsky

[57] ABSTRACT

The invention constitutes a dilating catheter for blood vessels in which the catheter is constituted of a hollow radiopaque tube designed to be snaked into the blood vessel and includes a working guide inside the tube which is both longitudinally movable and rotatable. The working guide is in the form of a flexible guide which arcs out from the longitudinal axis at the distal end and rotate in three dimensions. The arc portion is designed to be located at a single point or at several points along the flexible guide, where a stenosis, i.e. vessel constriction, is located. The guide rotates to distend the tube and thereby the blood vessel at the stenosis location. The guide is connected to a rotational drive, through a speed reducer. It is also connected to a gauge which measures the mechanical resistance of the guide to rotation and to an integrating meter which integrates the mechanical resistance to rotation, to provide the physician with interactive control over the dilation process. In a preferred embodiment, there are a pair of tubes and a pair of guides in which the respective arcs of the guides are turned 180° relative to one another and which operate in tandem.

12 Claims, 2 Drawing Sheets

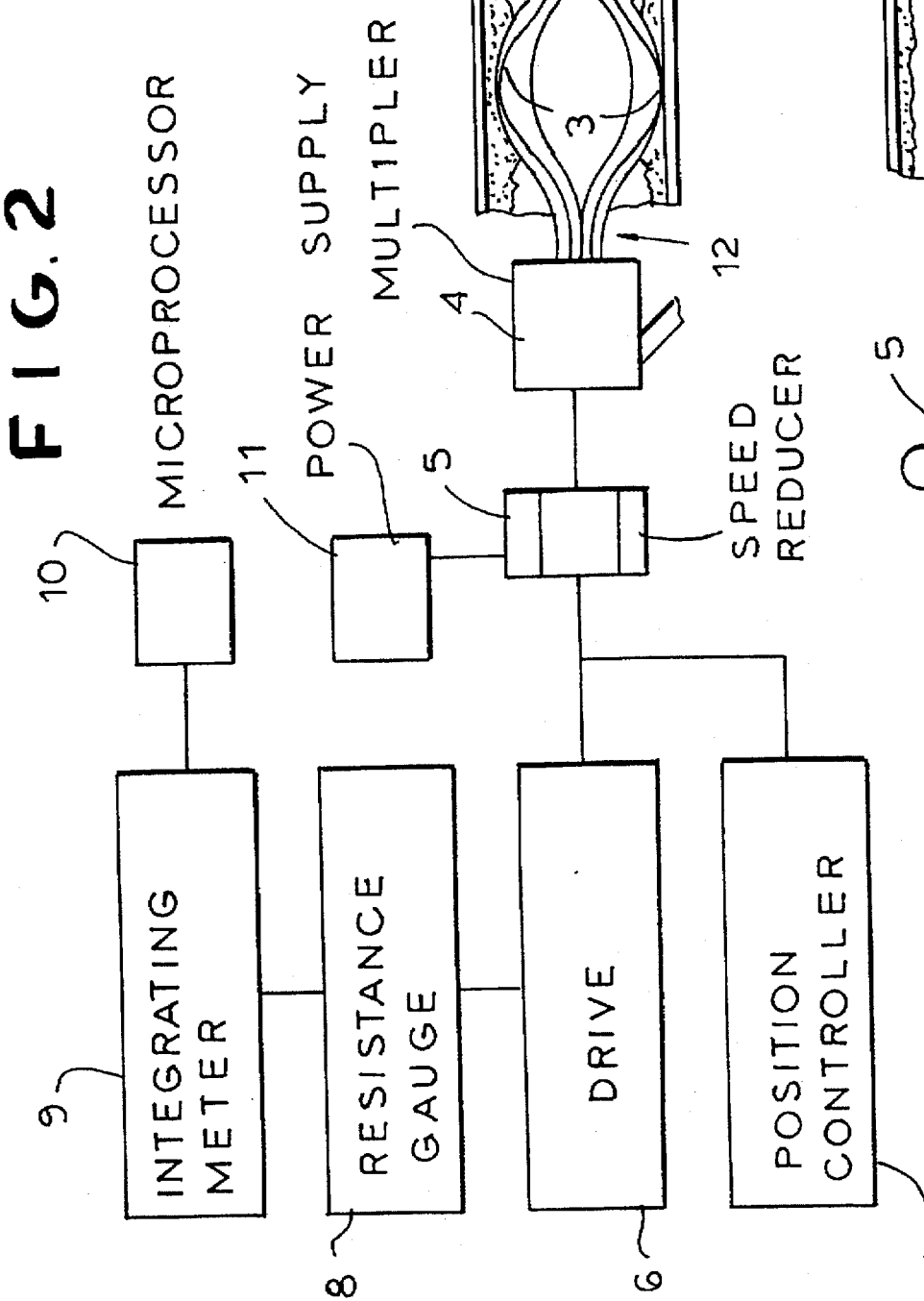

DEVICE AND METHOD FOR DYNAMIC DILATION OF HOLLOW ORGANS WITH ACTIVE PERFUSION AND EXTRACTION

BACKGROUND OF THE INVENTION

This application is based on and entitled to the priority of Provisional application Serial No. 60/002,244, filed Jun. 19, 1995.

The present invention relates to the field of medical technology and, in particular, to a device for use in cardiovascular surgery for restoring the lumen of a constricted blood vessel, as well as for dilation of the genital organs, uterine tubes, ureters, etc.

The prior art includes the well known balloon method for dilating hollow organs, such as blood vessels, using balloon angioplasty accompanied with active perfusion. Nonetheless, the conventional balloon dilation methods lack the capability of monitoring and controlling the intensity of the forces which are applied on the pathological focus inside the lumen of blood vessel. The inflatable balloon's energy is distributed over a wide area, so that tensile stress developing in the walls of the healthy portion of the blood vessel become greater than the tensile stress applied directly to the constricted part of the vessel. This occurs because of the balloon's different radii of curvature at the healthy and constricted parts of the blood vessel. As a result, internal rupturing of the wall tissue of the vessel occurs in the healthy part of the blood vessel, which manifests itself as an enlargement of the vessel's diameter and a weakening of its wall structure, which is highly undesirable.

A further disadvantage of balloon dilation techniques ensues from its inability to perform dilation in hollow organs which have variable diameters. There is no feedback information concerning the stress applied to the vessel wall during the dilation process. Also, the balloon catheter's lumen diameter fills the blood vessel and thereby severely limits the volume of active perfusion. There exists in the field a long felt, but unmet need to be able to concentrate and limit the dilation forces on and to the pathological site and to provide the physician with interactive control over the dilation process.

SUMMARY OF THE INVENTION

Accordingly, it is an object of the present invention to provide a dilation device which provides a diverse array of functional capabilities, including dynamic dilation of blood vessels of various diameters.

It is a further object of the present invention to provide the dilation device that includes the ability to handle the dilation of vessels which have various degrees of constrictions along their entire lengths.

It is a further object of the present invention to provide a blood vessel dilation device which readily permits and promotes the maintenance of blood flow and the monitoring and controlling of the working dilation forces with concommitment active perfusion.

It is yet another object of the present invention to provide a dilation device which is simple in construction and easy to use and maintain.

The foregoing and numerous other objects of the invention are realized with a dilating catheter which includes a tube for insertion into a body vessel, such as a blood vessel. A flexible guide inside the tube includes an arc portion, i.e. a bulging out portion, which is capable of being positioned at a desired location inside the tube. A driving device rotates the guide, including its arc portion, inside the tube, in manner which distends the tube so as to treat a constricted portion of the body vessel, i.e. a stenosis. To provide a physician with interactive control, a gauge is provided in coupling relation to the guide to measure mechanical resistance to rotation encountered by the guide. An integrating meter coupled to the gauge serves to integrate the value of the dilation forces experienced by the guide.

Preferred features of the invention include the provision of a tachometer to provide the physician with an indication of the speed of rotation of the flexible guide inside the tube and a microprocessor system for controlling the overall operation. Inherently, the rotation of the guide produces at the site of the arc a bulge which travels circumferentially and acts directly on the blood vessel at the site of the stenosis. The rotation of the bulge produces a turbine effect which, depending on the direction of rotation, promotes either perfusion or extraction of released matter from the blood vessel.

Other features of the dilating catheter of the present invention include a current meter for measuring the driving device's current, to provide an indication of the resistance to rotation in units of force. A more elaborate version of the dilating catheter includes two tubes, each with its own flexible guide therein, so as to simultaneously dilate the blood vessel at two different circumferential locations thereof.

Other features and advantages of the present invention will become apparent from the following description of the invention which refers to the accompanying drawings.

BRIEF DESCRIPTION OF THE DRAWINGS

FIG. 2 is both a block diagram and a cross-section through different portions of a second embodiment of the present invention.

FIG. 3 illustrates the manner of operation of the dilation device of FIG. 1.

DETAILED DESCRIPTION OF THE INVENTION

Figure 1:
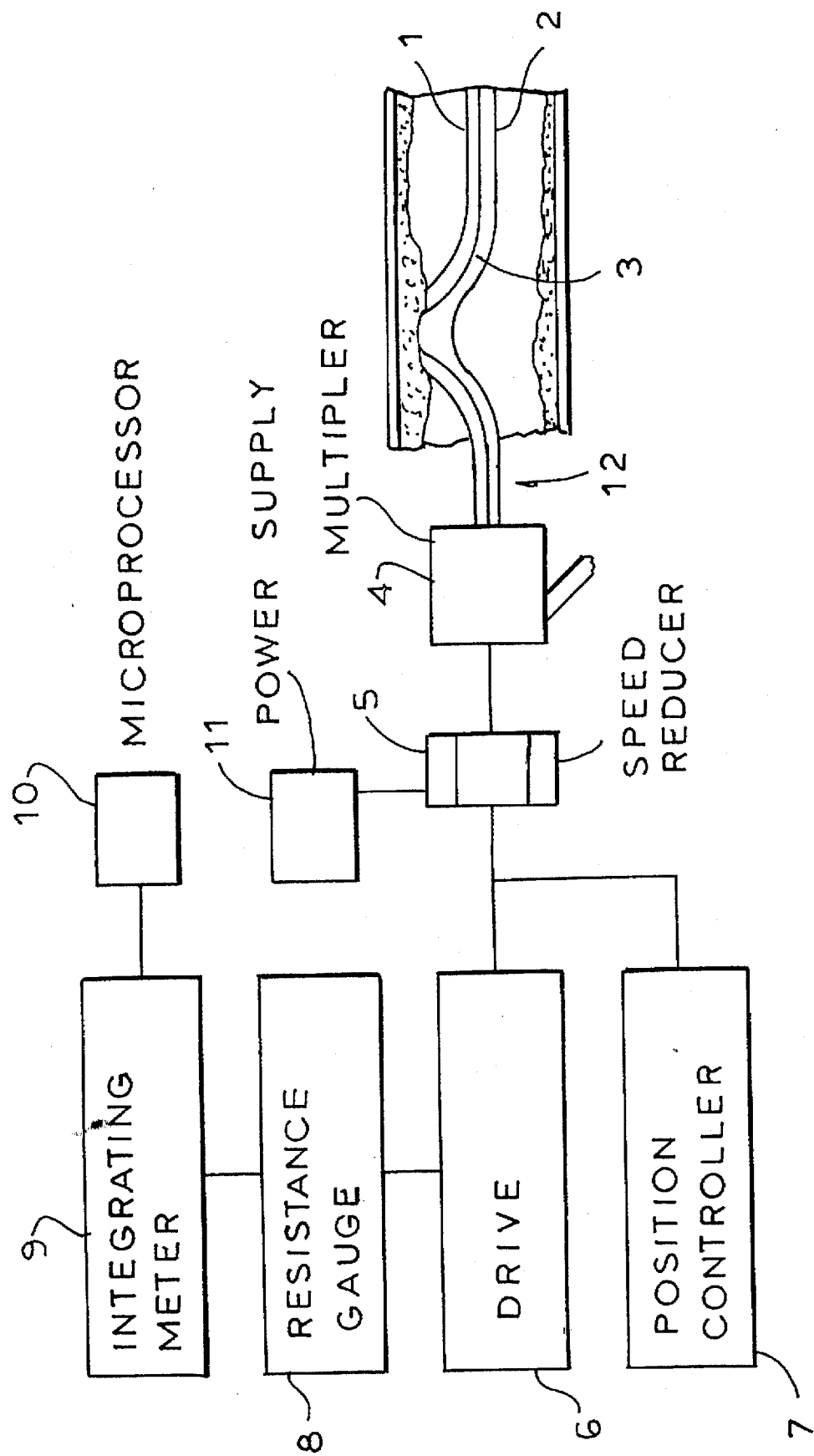
FIG. 1 is both a block diagram and a cross-section through different portions of a first embodiment of the present invention.

The dilation catheter 12 of the present invention includes, as illustrated in FIG. 1, a hollow, elongated elastic tube 1 which is designed to be snaked into a body vessel, such as a blood vessel, and which extends along an axial axis 14 thereof. A flexible guide 2 having at the distal end thereof an arc 3 is disposed inside the hollow tube 1, coaxially therewith. The guide 2 is connected, via a multiplexer 4 and a speed reducer 5, to a drive 6 which selectively rotates and/or moves the guide 2 lengthwise, i.e. axially, within the tube 1. The direction of rotation can be selected to be clockwise or counterclockwise determining, as shall be explained further on, whether perfusion is promoted or whether the device is operated to extract foreign matter from the vessel.

The drive 6 is further connected to a rotation resistance gauge 8, which measures the guide's mechanical resistance to rotation. This resistance varies of course with the degree of stenosis at the site where the arc 3 of the flexible guide 2 is currently rotating. The gauge 8 is graduated in units of force and also feeds its output signal to an integrating meter 9 which integrates the dilation forces. The overall catheter system 12 is coupled with and controlled by a microprocessor system 10 which is connected to the integrating meter 9.

Power is provided from a regulated power supply 11. The construction of the catheter 12 illustrated in FIG. 1 produces dynamic dilation and is instrumental in carrying out the process of dilating constricted blood vessels.

In operation, the catheter 12 is inserted into the blood vessel according to Seldinger's standard technique, until the arc portion 3 of the guide 2 is located in and around the vicinity of the stenosis in the blood vessel. However, before reaching the stenosis, the guide 2 is set rotating by the drive 6 in order to measure with the unit 8 the mechanical resistance to rotation in a healthy part of the blood vessel. The microprocessor 10 thus obtains a measure of the force and resistance to expansion in a healthy part of the vessel. The mechanical resistance to rotation at the healthy part is used as a reference value for assessing the degree of stenosis in the blood vessel of the patient being examined. The subsequent results of the dilation process of the constricted vessel are later compared and evaluated in relation to this measured, reference value.

Thereafter, the guide 2 is moved forward into the constricted portion of the vessel until the arc 3 contacts the stenosis that requires dilation. The guide 2 is then set rotating, continuously distending the wall of the stationary hollow tube 1 radially outwardly. This results in a circumferentially travelling bulge in the wall of the hollow tube 1 which acts on and thereby distend the inner surface of the blood vessel along the entire profile of the circle generated by the arc 3 of the guide 2 as it is rotating.

At a rotational velocity in the range of from 300 to 18,000 RPM, the arc 3 of the guide 2 is subjected to a centrifugal force which produces an additional mechanical effect on the wall of the tube 1, and through it, on the inner surfaces of the walls of the blood vessel. Dilation occurs as a result of both the circumferentially travelling bulge in the hollow tube 1 which results from eccentricity of the arc 3 and the rotational momentum of this bulge. This effect is set in motion and is fully controllable by the physician through control of the electrical drive 6. Due to a certain retained rigidity of the blood vessel wall, which requires a certain response time before it moves, the blood vessel does not simply move transversely in response to the rotation of the guide 2. Rather, the high rotational speed of the guide 2 coupled with the comparatively slow response time to bending of the blood vessel assure that the stenosis is internally flattened, instead of the vessel as a whole bending in response to the circumferentially travelling bulge.

As a result of the elastic deformation of the catheter tube which incorporates the guide, the device of the invention produces a dynamic wave which is driven against the blood vessel wall, distending it as required. The guide 2, as noted above, rotates and moves three-dimensionally, while the body of the catheter as a whole remains substantially fixed, i.e. stationary. The rotation of the catheter's flexible guide 2 creates a system of dynamic patterns having a great variety of three dimensional, symmetric motions. As a result of the dynamic properties of the device, these patterns can adjust themselves to the vessel's lumen in accordance with the vessel's diameter. The profile of the dynamic pattern at its outermost extension, creates, owing in part to the centrifugal forces, dynamic compression forces and circular expansion forces on the blood vessel walls in response to the motion of the guide, causing alternatively stretching and relaxing of the blood vessel wall. Thus, the forces of expansion and compression cause dilation of the part of the vessel that is the site of the stenosis. Because of dynamic compression at the area of the pathological focus, the amount of fluid flowing through the lumen of the vessel is normally lower, resulting in a reduction in intercellular fluid flow.

However, the instant invention makes it possible to bring about a stronger and more directed mechanical effect on the vessel wall over a smaller radius of curvature, i.e. where the area of the pathological focus is situated, for example, atherosclerotic plaque, which would otherwise encompass a healthy part of the vessel. The invention promotes fluid flow. That is, the inner profile (radii) of the dynamic patterns resulting from the rotating flexible guide create a turbine effect which influences the movement of blood from the locations just upstream and downstream of the stenosis area. More specifically, the controlled dynamic pattern created as a result of the guide's rotation causes compression and expansion, as noted above, along the outer profile of the dynamic pattern and creates a turbine effect along the inner profile of the dynamic pattern. By controlling the three dimensional wave, the physician is able to cause changes in the directional rotational motion of the deformed guide, setting the elastic deformation of the catheter body to proceed clockwise or counterclockwise (maintaining the dynamic pattern's configuration and the effect of expansion and compression on the blood vessel wall). The rotational direction sets the direction of the turbine effect and of the dynamic pattern. This makes it possible to use the device of the invention for promoting perfusion and/or for improving extractions of newly formed thrombus' from the vessel's lumen.

In the process of carrying out the catheter dilation, the value of the mechanical resistance to rotation is constantly monitored by observing the unit 8 and by further observing the cumulative mechanical force acting on the blood vessel wall through reading of the unit 9. The unit 9 operates by summing, i.e. integrating, the forces encountered by the guide 2 as they occur, for as many times and for as long as the guide 2 continues to rotates. This integration proceeds during the entire time that the operation is performed. It makes it possible to monitor and assure that the amount of force and dilation being applied does not exceed the limits of the vessel wall's breaking strength, to avoid and preclude rupturing the same.

The vessel is considered dilated if the value of the mechanical rotational resistance is equal to or less than the value of the mechanical resistance in the healthy part of the vessel that has been recorded at the initial stage of the operation. The microprocessor system 10 adjusts the rotational speed of the speed reducer 5 in response to the information supplied by the dilation forces meter 9.

When dilation is performed by means of the device and system of the present invention, local blood flow is maintained because the lumen of the vessel is not totally blocked, as with the known balloon method. In addition, active perfusion is also carried out without hinderance due to the aforementioned turbine effect.

In accordance with a second embodiment of the present invention (FIG. 2), the catheter of the present invention comprises two elastic tubes 1, each carrying its own respective flexible guide 2 and arc 3. Preferably, the peripheral radial ends of the arc are turned away from one another, lying in the same plane and facing 180° apart. The proximal ends of the guides 2 are connected, as before, via the multiplexer 4 and speed reducer 5, to the rotational drive 6 and the axial position controller 7. The rotational drives 6 are both connected to the gauge 8 which measures mechanical resistance to rotation and to the integrating meter 9 which integrates the dilation forces as previously described.

The procedure for using the catheter of the second embodiment is generally similar to the procedure for using and working with the catheter which has only a single guide. In this case, the distending process is faster and therefore the time the operation requires is shorter, thus subjecting the blood vessel to a shorter treatment time.

Once the desired distention effect on the blood vessel has been achieved, the electrical drives 6 and 7 are shut off, and the guide 2 is disconnected and withdrawn from the tube 1. The last step requires removal of tube from the recanalized vessel and the procedure is concluded with the application of a compression bandage to the body at the point of insertion of the catheter.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A dilating catheter, comprising:
   at least one for insertion into a body vessel;
   a flexible guide inside each tube, each guide including an arc portion capable of being positioned at a desired location inside the tube;
   a driving device for rotating the guide including the arc portion thereof inside the tube, said arc portion applying force to the tube so as to distend a potion of the tube radially outwardly to treat a constricted portion of the body vessel; and
   a gauge connected to the guide and effective for measuring mechanical resistance to rotation encountered by the guide.

2. The dilating catheter of claim 1, including an integrating meter coupled to the gauge for integrating the value of the dilation forces encountered by the guide.

3. The dilating catheter of claim 2, further including a tachometer coupled to the guide for providing an indication of the rotational speed of the guide.

4. The dilating catheter of claim 3, in which the driving device is capable of turning the guide in a first direction and in a second direction to respectively promote perfusion and extraction in the body vessel.

5. The dilating catheter of claim 3, in which the integrating meter comprises an adder for adding the values of mechanical resistance to rotation during each rotation of the guide and for providing a reading graduated in units of force.

6. The dilating catheter of claim 1, in which the tube comprises a body in the form of a hollow radiopaque tube.

7. The dilating catheter of claim 1, in which the tube, the guide and driving device are configured so that rotation of the guide selectively promotes perfusion of liquid through the body vessel and extraction of released matter from the vessel.

8. The dilating catheter of claim 1, in which the at least one tube comprises a first tube and a second tube, each of the first and second tubes having its respective flexible guide so as to act at any given moment of time at two different circumferential locations of the body vessel.

9. The dilating catheter of claim 8, in which the arc of each of the respective flexible guides points in directions which are circumferentially about 180° apart relative to one another.

10. The dilating catheter of claim 1, further including a speed reducer coupled with the driving device.

11. The dilating catheter of claim 1, in which the gauge comprises a current meter for measuring the driving device's current and for providing an indication of the resistance to rotation in units of force.

12. The dilating catheter of claim 1, further including a microprocessor data-analysis system coupled to the integrating meter for providing positive and negative feedback control.

* * * * *